US00PP29845P3

(12) United States Plant Patent
Eggleton

(10) Patent No.: US PP29,845 P3
(45) Date of Patent: Nov. 13, 2018

(54) ***SALVIA* PLANT NAMED 'IB304-2 PURPLE'**

(50) Latin Name: *Salvia hybrida*
Varietal Denomination: IB304-2 PURPLE

(71) Applicant: Steve Eggleton, Wonga Park (AU)

(72) Inventor: Steve Eggleton, Wonga Park (AU)

( * ) Notice: Subject to any disclaimer, the term of this patent is extended or adjusted under 35 U.S.C. 154(b) by 59 days.

(21) Appl. No.: 15/530,736

(22) Filed: Feb. 21, 2017

(65) Prior Publication Data

US 2018/0242505 P1 Aug. 23, 2018

(51) Int. Cl.
*A01H 5/02* (2018.01)
*A01H 6/50* (2018.01)

(52) U.S. Cl.
USPC ..... Plt./475
CPC ..... *A01H 6/508* (2018.05)

(58) Field of Classification Search
USPC ..... Plt./263.1, 475
See application file for complete search history.

*Primary Examiner* — Susan McCormick Ewoldt
*Assistant Examiner* — Karen M Redden
(74) *Attorney, Agent, or Firm* — Cassandra Bright

(57) ABSTRACT

A new and distinct *Salvia* cultivar named 'IB304-2 PURPLE' is disclosed, characterized by a dense, bushy plant habit, strong peduncles, medium purple-violet colored flowers. Flowers have a calyx flushed with dark anothocyanin. The new variety is a *Salvia*, normally produced as an outdoor garden or container plant.

2 Drawing Sheets

Figure 1:
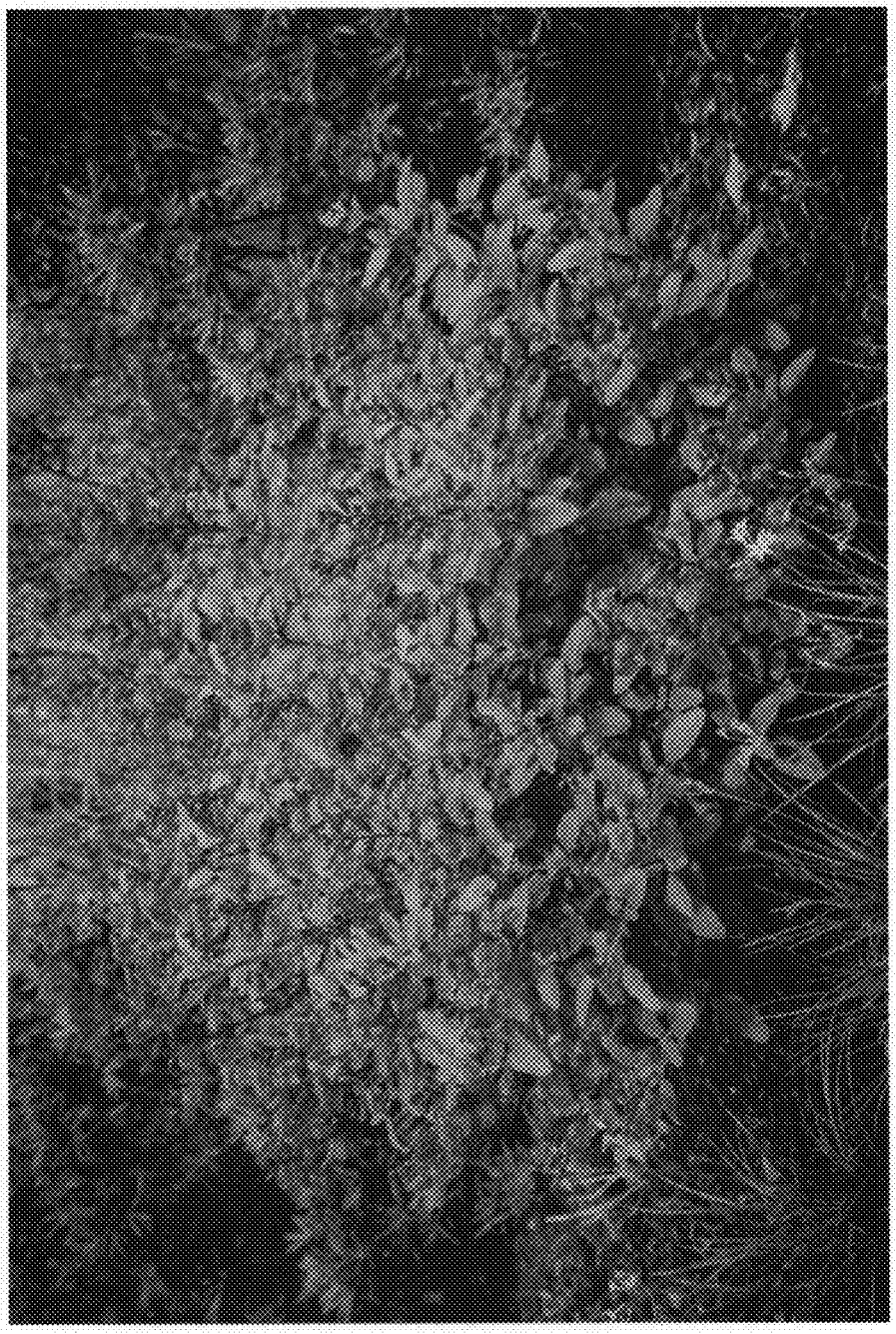

Latin name of the genus and species: *Salvia hybrida*.
Variety denomination: 'IB304-2 PURPLE'.

BACKGROUND OF THE INVENTION

The new *Salvia* cultivar is a product of a planned breeding program conducted by the inventor, Steve Eggleton, in Wonga Park, Victoria, Australia. The objective of the breeding program was to produce new *Salvia* varieties with denser plant habits, strong garden performance, in a range of flower colors. The crossing resulting in this new variety was made during February of 2012.

The parent variety is *Salvia hybrida* 'Eggben006', unpatented. The pollen parent is *Salvia* 'Ultra Violet', U.S. Plant Pat. No. 21,411. The new variety was identified as a potentially interesting selection in February 2013 at a research greenhouse in Wonga Park, Australia. The breeder propagated and made further observations regarding stability and quality of the new variety, making the final selection in April of 2014.

Asexual reproduction of the new cultivar 'IB304-2 PURPLE' by vegetative cuttings was first performed during February 2013, at a research greenhouse in Wonga Park, Australia. Subsequent propagation has shown that the unique features of this cultivar are stable and reproduced true to type on most than six successive generations.

SUMMARY OF THE INVENTION

The cultivar 'IB304-2 PURPLE' has not been observed under all possible environmental conditions. The phenotype may vary somewhat with variations in environment such as temperature, day length, and light intensity, without, however, any variance in genotype.

The following traits have been repeatedly observed and are determined to be the unique characteristics of 'IB304-2 PURPLE' These characteristics in combination distinguish 'IB304-2 PURPLE' as a new and distinct *Salvia* cultivar:

1. Bushy plant habit.
2. Medium Purple-Violet flower color.

3. Sturdy inflorescence.
4. Dense plant habit.
5. Dark anthocyanin coloration of calyx.

PARENT COMPARISON

Plants of the new cultivar 'IB304-2 PURPLE' are similar to plants of the seed parent, in most horticultural characteristics, however, plants of the new cultivar 'IB304-2 PURPLE' differ in the following:

1. Flower color of the new variety is purple-violet, flower color of the seed parent is white.

Plants of the new cultivar 'IB304-2 PURPLE' are similar to plants of the pollen parent, in most horticultural characteristics, however, plants of the new cultivar 'IB304-2 PURPLE' differ in the following:

1. Flower color of the new variety is medium violet-purple, flower color of the pollen parent is dark violet-purple.
2. Plant habit of the new variety is denser, with more branches per plant.
3. Venation of the new variety is prominent, venation of the pollen parent is very weak.
4. The central eye in flowers of the new variety is small, this feature in the pollen variety is very weak or absent.

COMMERCIAL COMPARISON

Plants of the new cultivar can be compared to the commercial variety *Salvia microphylla* 'So Cool Lilac', unpatented. The two *Salvia* varieties are very similar in most horticultural characteristics, however, the new variety differs in the following;

1. Flower color of the new variety is Purple-Violet N82A and N82B. Flower color of this comparator is Violet-Blue 92A and 92B.
2. The central eye in flowers of the new variety is small, this feature in this comparator is medium.

Plants of the new cultivar can be compared to the commercial variety *Salvia microphylla* 'So Cool Violet', unpatented. The two *Salvia* varieties are very similar in most horticultural characteristics, however, the new variety differs in the following;

1. Flower color of the new variety is Purple-Violet N82A and N82B. Flower color of this comparator is Violet N87A.
2. The central eye in flowers of the new variety is small, this feature in this comparator is very small to absent.

Plants of the new cultivar can be compared to the commercial variety *Salvia hybrida* 'Mesa Purple', unpatented. The two *Salvia* varieties are very similar in most horticultural characteristics, however, the new variety differs in the following;

1. Flower color of the new variety is medium purple-violet, flower color of this comparator is dark purple-violet.
2. Foliage shape of the new variety is narrow ovate, foliage shape of this comparator is broadly ovate.

Plants of the new cultivar can be compared to the commercial variety *Salvia* hybrid 'Mes Azure', U.S. Plant Pat. No. 21,097. The two *Salvia* varieties are very similar in most horticultural characteristics, however, the new variety differs in the following;

1. Flower color of the new variety is Purple-Violet N82A and N82B. Mature flower color of this comparator is Violet-N87B.
2. The central eye in flowers of the new variety is small, this feature in this comparator is medium to large.

BRIEF DESCRIPTION OF THE PHOTOGRAPHS

The accompanying photograph in FIG. 1 illustrates in full color a typical plant of 'IB304-2 PURPLE'.

Figure 2:
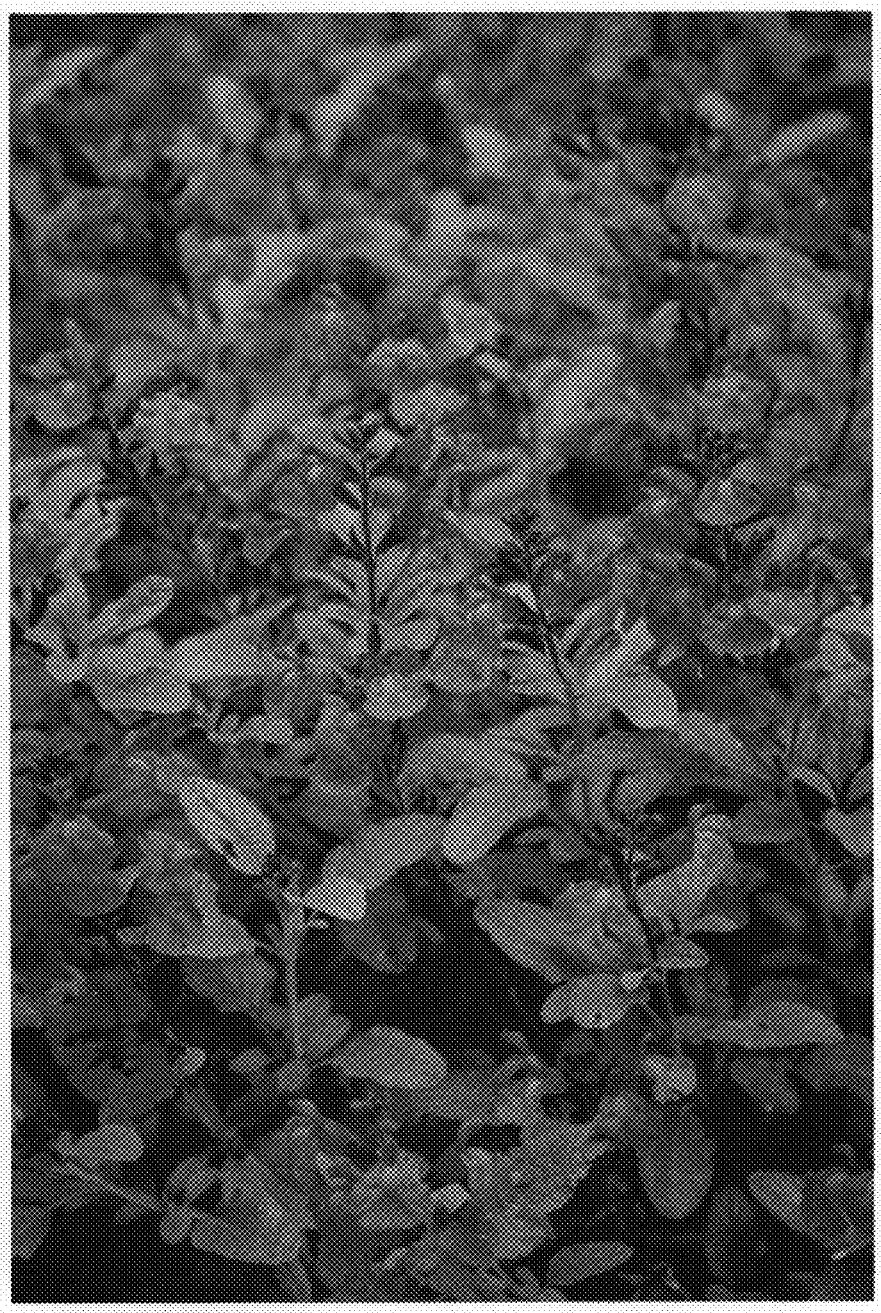

FIG. 2 illustrates in full color typical flowers of 'IB304-2 PURPLE'.

The plant was grown outdoors, in Wonga Park, Australia. Age of the plant photographed is approximately 50 weeks from an unrooted cutting. The photographs were taken using conventional techniques and although colors may appear different from actual colors due to light reflectance it is as accurate as possible by conventional photographic techniques.

DETAILED BOTANICAL DESCRIPTION

In the following description, color references are made to The Royal Horticultural Society Colour Chart 2007 except where general terms of ordinary dictionary significance are used. The following observations and measurements describe 'IB304-2 PURPLE' plants grown outdoors in Wonga Park, Australia. The growing temperature ranged from approximately 5° C. to 35° C. Measurements and numerical values represent averages of typical plant types. Botanical classification: *Salvia hybrida* 'IB304-2 PURPLE'.

PROPAGATION

Time to initiate roots: About 5-8 days at approximately 25° C.

Root description: Fine, densely fibrous.

Time to produce a rooted cutting: About 21 days at 25° C.

PLANT

Growth habit: Upright, bushy annual.

Height: Approximately 70 cm.

Plant spread: Approximately 100 cm.

Growth rate: Rapid.

Branching characteristics: Free-branching, Approximately 10 to 14 primary branches.

Length of primary lateral branches: Approximately 50 to 60 cm.

Diameter of lateral branches: Approximately 0.4 cm.

Quantity of lateral branches: About 12 to 18.

Stem:

*Color*.—Near RHS Green 138B, flushed with Greyed-Purple N187A.

*Pubescence*.—Minute pubescence.

Internode length: Approximately 2.0 to 2.5 cm.

Age of plant described: Approximately 50 weeks from an unrooted cutting.

FOLIAGE

Leaf:

*Arrangement*.—Opposite.

*Quantity*.—Approximately 16 to 20 fully expanded per main branch.

*Average length*.—Approximately 5.2 cm., including petiole.

*Average width*.—Approximately 2.3 cm.

*Shape of blade*.—Narrow ovate.

*Apex*.—Obtuse.

*Base*.—Obtuse to nearly truncate.

*Attachment*.—Stalked.

*Margin*.—Crenate.

*Texture of top surface*.—Matte, minute, coarse pubescence. Reticulate veins.

*Texture of bottom surface*.—Matte, minute, coarse pubescence.

*Color*.—Young foliage upper side: Near RHS Green 137A. Young foliage under side: Near RHS Green 137B. Mature foliage upper side: Near RHS Green 137B. Mature foliage under side: Near RHS Green 138A.

*Venation*.—Type: Pinnate. Venation color upper side: Near RHS Yellow-Green 144A. Venation color under side: Near RHS Green 143C.

*Petiole*.—Average Length: Approximately 0.8 cm. Diameter: Approximately 0.1 cm. Color: Near Yellow-Green 144A.

FLOWER

Natural flowering season: Flowering from early Spring through late Summer.

Inflorescence type and habit: Flowers arranged in verticillasters on spikes.

Flower longevity on plant: Individual flowers last approximately 1 week on the plant. Each spike lasts approximately 7 weeks with flowers.

Quantity of flowers: About 8 to 12 buds and 6 to 10 fully opened flowers per spike, at one time. Mature plants have approximately 10 to 20 spikes.

Spike size:

*Diameter*.—Approximately 7.0 cm.

*Height*.—Approximately 8 to 15 cm.

Individual flowers:

Size:

*Diameter*.—Approximately 2.5 cm.

*Length*.—Approximately 3.0 cm.

Persistence: Non-persistent.

Fragrance: Moderate, typical *Salvia* scent.

Corolla:

*Petal arrangement*.—The corolla is sympetalous and typically bilabiate with 2 small, highly fused lobes forming an upper lip and 3 larger highly fused lobes forming a lower lip.

*Margin*.—Nearly entire, slightly scalloped.

*Tip shape*.—Upper lip tip retuse, lower lip tip rounded with scallops.

*Length*.—Upper lip Approximately 1.3 cm, lower lip Approximately 1.8 cm. Tube length Approximately 2.1 cm.

*Width*.—Upper lip Approximately 0.4 cm, lower lip Approximately 2.5 cm. Tube width Approximately 0.8 cm.

*Texture*.—Upper lip: Highly pubescent on exterior surface. Interior surface glabrous. Lower lip: Glabrous all surfaces.

Color:

*Upper lip*.—When opening: Inner surface: Background color Near RHS Purple-Violet N82A. Outer surface: Background color Near RHS Purple-Violet N82A. Fully opened: Inner surface: RHS Purple-Violet N82A. Outer surface: RHS Purple-Violet N82A. Fading: Inner surface: RHS Purple-Violet N82B. Outer surface: RHS Purple-Violet N82B.

Color:

*Lower lip*.—When opening: Inner surface: RHS Purple-Violet N82B. Outer surface: RHS Purple-Violet N82B. Fully opened: Inner surface: RHS Purple-Violet N82B. Outer surface: RHS Purple-Violet N82B. Fading: Inner surface: Near RHS Purple-Violet N82B. Outer surface: Near RHS Purple-Violet N82B.

Color:

*Tube*.—When opening: Inner surface: Near RHS Purple-Violet N82C. Outer surface: Near RHS Purple-Violet N82A. Fully opened: Inner surface: Near RHS Purple-Violet N82D. Outer surface: Near RHS Purple-Violet N82B. Fading: Inner surface: Near RHS Purple-Violet N82D. Outer surface: Near RHS Purple-Violet N82B.

Bud:

*Shape*.—Ovoid.

*Length*.—Approximately 1.4 cm.

*Diameter*.—Approximately 0.9 cm.

*Color*.—Near RHS Purple-Violet N82A.

Calyx:

*Length*.—Approximately 1.5 cm.

*Diameter*.—Approximately 0.08 cm.

*Shape*.—Tubular.

Sepals:

*Shape*.—Quantity per flower: 3, fused to form a tube.

*Unfused apex*.—Length: Approximately 0.7 cm. Width: Approximately 0.5 cm. Margin: Entire. Apex: Acute. Texture: Pubescent. Color: Immature: Near RHS Greyed-Purple 187C, flushed Purple N79A. Mature: Near RHS Purple N77A.

Peduncle:

*Length*.—Average range 3.0 to 6.0 cm.

*Diameter*.—0.3 cm.

*Color*.—Near RHS Purple 79A.

*Orientation*.—Upright, straight.

*Strength*.—Strong.

*Texture*.—Pubescent.

Pedicels:

*Length*.—Average 0.2 cm.

*Diameter*.—0.1 cm.

*Color*.—Near RHS Purple 79A.

*Orientation*.—Straight, approximately 45 degree angle from attachment.

*Strength*.—Flexible.

*Texture*.—Pubescent.

REPRODUCTIVE ORGANS

Stamens:

*Number*.—2.

*Filament length*.—Approximately 1.2, approximately .6 cm of length fused to petal.

*Filament color*.—Near RHS White N155B.

Anthers:

*Shape*.—Very narrowly elliptic.

*Length*.—Approximately 3 mm.

*Color*.—Near RHS Greyed-White 156A.

*Pollen*.—Scant colored near Greyed-White 156D.

Pistil:

*Number*.—1.

*Length*.—Approximately 2.2 cm.

*Color*.—Near RHS White N155A.

*Stigma*.—Shape: Linear, curled. Color: Near RHS Purple 79A. Ovary color: Near RHS Green-Yellow 1B.

OTHER CHARACTERISTICS

Seeds and fruits: Not observed to date.

Disease/pest resistance: Neither resistance nor susceptibility to pathogens and pests common to *Salvia* have been observed.

Temperature tolerance: The new variety tolerates temperatures between 5 to 35° C.

What is claimed is:

1. A new and distinct cultivar of *Salvia* plant named 'IB304-2 PURPLE' as herein illustrated and described.

* * * * *